US010561491B2

(12) United States Patent
Zhao

(10) Patent No.: US 10,561,491 B2
(45) Date of Patent: Feb. 18, 2020

(54) REDUCED GLARE INTRAOCULAR LENS

(71) Applicant: ABBOTT MEDICAL OPTICS INC., Santa Ana, CA (US)

(72) Inventor: Huawei Zhao, Irvine, CA (US)

(73) Assignee: Johnson & Johnson Surgical Vision, Inc., Santa Ana, CA (US)

(*) Notice: Subject to any disclaimer, the term of this patent is extended or adjusted under 35 U.S.C. 154(b) by 38 days.

(21) Appl. No.: 15/712,048

(22) Filed: Sep. 21, 2017

(65) Prior Publication Data

US 2018/0028307 A1 Feb. 1, 2018

Related U.S. Application Data

(63) Continuation of application No. 13/931,078, filed on Jun. 28, 2013, now Pat. No. 9,770,325.

(60) Provisional application No. 61/666,413, filed on Jun. 29, 2012.

(51) Int. Cl.
*A61F 2/16* (2006.01)
*G02C 7/14* (2006.01)

(52) U.S. Cl.
CPC .............. *A61F 2/1613* (2013.01); *A61F 2/16* (2013.01); *A61F 2/1637* (2013.01); *A61F 2002/1696* (2015.04); *G02C 7/14* (2013.01)

(58) Field of Classification Search
CPC ... A61F 2002/1696; G02C 7/04; G02C 7/042; G02C 7/044
See application file for complete search history.

(56) References Cited

U.S. PATENT DOCUMENTS

| 4,676,791 A | * | 6/1987 | LeMaster | A61F 2/1613 623/6.17 |
| 5,480,950 A | | 1/1996 | Wang et al. | |
| 5,578,081 A | * | 11/1996 | McDonald | A61F 2/1629 623/6.17 |
| 5,702,441 A | | 12/1997 | Zhou | |
| 5,755,786 A | * | 5/1998 | Woffinden | A61F 2/16 351/159.08 |
| 8,696,746 B2 | * | 4/2014 | Wanders | A61F 2/1602 623/6.27 |
| 2003/0114926 A1 | * | 6/2003 | Paul | A61F 2/1613 623/6.16 |
| 2003/0130733 A1 | | 7/2003 | Paul et al. | |
| 2003/0144733 A1 | | 7/2003 | Brady et al. | |
| 2005/0060031 A1 | | 3/2005 | Coroneo et al. | |
| 2007/0244560 A1 | * | 10/2007 | Ossipov | A61F 2/1601 623/6.14 |

(Continued)

OTHER PUBLICATIONS

Advisory Action dated Nov. 12, 2015 for U.S. Appl. No. 13/931,078, filed Jun. 28, 2013.

(Continued)

*Primary Examiner* — David H Willse
*Assistant Examiner* — Tiffany Shipmon
(74) *Attorney, Agent, or Firm* — Johnson & Johnson Surgical Vision, Inc.

(57) ABSTRACT

An intraocular lens for reducing aberrant optical effects includes an anterior surface, a posterior surface and a peripheral region/zone disposed about a central optical axis. The peripheral region/zone has an inflection region/transition area that is inclined with respect to the anterior surface at an angle between about 40 degrees and 120 degrees with respect to the optical axis.

11 Claims, 3 Drawing Sheets

(56) References Cited

U.S. PATENT DOCUMENTS

| | | | | |
|---|---|---|---|---|
| 2008/0077239 A1* | 3/2008 | Zickler | ............ | A61F 2/1613 623/6.16 |
| 2008/0269882 A1* | 10/2008 | Simpson | ............ | A61F 2/1613 623/6.17 |
| 2008/0269886 A1* | 10/2008 | Simpson | ............ | A61F 2/1654 623/6.25 |
| 2009/0018651 A1* | 1/2009 | Zhang | ............ | A61F 2/1613 623/6.17 |
| 2009/0033863 A1 | 2/2009 | Blum et al. | | |
| 2014/0180408 A1 | 6/2014 | Angelopoulos et al. | | |

OTHER PUBLICATIONS

Advisory Action dated Nov. 22, 2016 for U.S. Appl. No. 13/931,078, filed Jun. 28, 2013.
Final Office Action dated Jul. 7, 2015 for U.S. Appl. No. 13/931,078, filed Jun. 28, 2013.
Final Office Action dated Sep. 8, 2016 for U.S. Appl. No. 13/931,078, filed Jun. 28, 2013.
Final Office Action dated Mar. 18, 2015 for U.S. Appl. No. 13/931,078, filed Jun. 28, 2013.
Final Office Action dated Mar. 27, 2015 for U.S. Appl. No. 13/931,140, filed Jun. 28, 2013.
International Search Report and Written Opinion for Application No. PCT/US2013/048670, dated Sep. 30, 2013, 15 pages.
International Search Report and Written Opinion for Application No. PCT/US2013/048682, dated Sep. 30, 2013, 14 pages.
Non-Final Office Action dated Oct. 13, 2015 for U.S. Appl. No. 13/931,140, filed Jun. 28, 2013.
Non-Final Office Action dated Jul. 22, 2014 for U.S. Appl. No. 13/931,078, filed Jun. 28, 2013.
Non-Final Office Action dated Oct. 24, 2014 for U.S. Appl. No. 13/931,140, filed Jun. 28, 2013.
Non-Final Office Action dated Feb. 26, 2016 for U.S. Appl. No. 13/931,078, filed Jun. 28, 2013.
Non-Final Office Action dated Dec. 29, 2016 for U.S. Appl. No. 13/931,078, filed Jun. 28, 2013.

* cited by examiner

REDUCED GLARE INTRAOCULAR LENS

CROSS-REFERENCES TO RELATED APPLICATIONS

This application is a continuation of and claims priority to U.S. application Ser. No. 13/931,078, filed Jun. 28, 2013, which claims priority to U.S. Application No. 61/666,413, filed on Jun. 29, 2012, the contents of which are incorporated herein by reference for all purposes. Full Paris Convention priority is hereby expressly reserved.

FIELD OF THE INVENTION

This application relates generally to intraocular lenses, and more specifically to intraocular lenses with reduced aberrant optical effects, such as reduced positive and/or negative dysphotopsia.

DESCRIPTION OF THE RELATED ART

A human eye can suffer diseases that impair a patient's vision. For instance, a cataract may increase the opacity of the natural crystalline lens, causing blindness. To restore the patient's vision, the opaque lens may be surgically removed and replaced with an artificial intraocular lens, or IOL. An IOL may also be implanted to treat presbyopia or for other elective ocular surgical procedures. The IOL can be an accommodating IOL, which can adjust its axial position and/or shape to vary the optical power within a range in response to muscle action in the eye. As a result, the patient can focus on objects in a range of distances from the eye, rather than at one discrete distance. The IOL may also be a multifocal IOL utilizing a refractive and/or diffractive surfaces resulting in multiple focal points.

Healthy phakic eyes typically have a non-compromised visual field of about 60 degrees in the nasal direction, 105 degrees in the temporal direction, 65 degrees in the superior direction, and 70 degrees in the inferior direction. With current IOLs, pseudophakic eyes may have reduced the field of view.

In addition, undesirable optical effects can arise after implantation of an IOL. One of the undesirable optical effects is dysphotopsia which is defined as the appearance of unwanted visible patterns. It is believed that light refracted into the IOL can reflect from a sharp or truncated edge of the IOL thereby causing glare, positive dysphotopsia, or other aberrant optical effects. Positive dysphotopsia can refer to the appearance of bright optical artifacts such as rings, halos, arcs or streaks. Negative dysphotopsia can refer to the appearance of dark shadows or lines in the field of vision. Negative dysphotopsia may occur when some light rays that enter the eye and are either (1) not incident on the IOL and pass by the IOL or (2) incident on the IOL edge, while immediately adjacent light rays enter the IOL and are refracted by and pass through the IOL onto the retina. Thus, IOLs that can reduce or mitigate aberrant optical effects, such as positive and/or negative dysphotopsia, as well as increase field of view are desirable.

SUMMARY OF THE INVENTION

The systems, methods and devices of the disclosure each have several innovative aspects, no single one of which is solely responsible for the desirable attributes disclosed herein.

Embodiments disclosed herein are directed to devices and methods for providing corrective vision in the event the natural lens is replace. In some embodiments, it would be desirable to have an artificial IOL that can reduce or mitigate dysphotopsia, or other aberrant optical effects and regain the phakic field of view.

In one aspect, an IOL is provided that can reduce or mitigate dysphotopsia. In IOLs, one of the causes of dysphotopsia is the interaction of light that is refracted by the IOL with the edge of the IOL. Accordingly, a possible solution to reduce or mitigate dysphotopsia is to design an IOL such that the edge of the IOL is outside the path of light rays entering the eye and incident on the IOL. In such a design since light rays incident on the edge of the IOL is minimized or eliminated, dysphotopsia can be reduce or eliminated. In various implementations, the IOL has an anterior surface and a posterior surface that are intersected by an optical axis. The anterior and posterior surfaces are joined by a peripheral region. Peripheral light from the side and behind a patient's eye enters the cornea refracting at a maximum angle of about $r_1$ degrees. These rays are incident on the anterior surface of the IOL and are refracted at a maximum angle of $r_2$ degrees. For a refractive surface, the peripheral region is inclined at an angle of inclination greater than $$sin^{-1}\left(\frac{n_2}{n_3}sinr_1\right),$$

where $n_3$ is the refractive index of the material of the intraocular lens, $n_2$ is the combined refractive index of the cornea and the aqueous humor. When the anterior and/or posterior surface contains a diffractive surface, formulas based on diffractive optics are applicable as known to those skilled in the art. The angle of inclination in this sense is defined with respect to an axis parallel to the central optical axis OA, intersecting the peripheral region at the inflection point and extending in the posterior direction from the inflection point. Additionally, the peripheral region may angle posteriorly from the anterior surface. By way of example, in a 20 Diopter IOL, the peripheral region may be inclined posteriorly and defined at an angle greater than about 40 degrees in order to prevent rays from striking the edge of the IOL.

In one preferred embodiment, an intraocular lens is comprised of an anterior optical surface extending peripherally from a central optical axis of the intraocular lens; a posterior optical surface extending peripherally from the central optical axis; and a peripheral zone disposed about and extending laterally from the anterior optical surface, the peripheral zone being inclined posteriorly from the anterior optical surface; wherein the extent of the posterior incline of the peripheral zone is sufficient to prevent aberrant optical effects from high angle optical rays directed posteriorly toward the intraocular lens and refracted by the anterior surface. The peripheral zone may comprise of a peripheral surface extending laterally and posteriorly from a point of inflection disposed between the anterior surface and the peripheral zone. The point of inflection may be disposed laterally from the central optical axis by a distance greater than the distance to the location of the optic where the rays of greatest divergence refracted into the eye by the cornea strike the anterior surface of the lens when implanted in the capsular bag of a patient's eye. The point of inflection may be disposed laterally of the optical axis by at least about 2 mm, and is preferably at least about 2.5 mm, but may be configured to match the capsular bag size which is typically up to at least about 5 mm. An angle may be provided between the peripheral surface and an axis extending posteriorly from the point of inflection disposed between the anterior surface and the peripheral zone, wherein the angle is greater than or equal to a maximum angle of refraction by the anterior surface of the rays of greatest divergence refracted into the eye by the cornea. The aforementioned angle may be greater than or equal to about 40 degrees and is preferably greater than or equal to about 55 degrees, and more preferably greater than or equal to about 60 degrees. Depending on the configuration, the angle may be as large as about 120 degrees. For a generally circular IOL embodiment, the diameter of the anterior surface of the lens as viewed from a top plan view is in the range of about 4 mm-9 mm and is preferably between about 7-9 mm or more preferably between about 8-9 mm. For a generally circular IOL embodiment, the diameter of the posterior surface of the lens as viewed from a top plan view is in the range of about 5 mm-11 mm and is preferably between about 8-11 mm or more preferably between about 9-11 mm.

In another preferred embodiment, the intraocular lens may be comprised of an anterior optical surface extending peripherally from a central optical axis of the intraocular lens; a posterior optical surface extending peripherally from the central optical axis; and a peripheral surface disposed about and extending laterally from the anterior optical surface, the peripheral surface being inclined posteriorly from the anterior optical surface; wherein the intraocular lens is configured to minimize dysphotopsia by preventing peripheral light rays from passing through the peripheral surface of the lens. The intraocular lens may be configured to minimize negative and/or positive dysphotopsia with the peripheral surface located laterally outward of the trajectory of peripheral light rays refracted by the anterior surface of the lens.

In another preferred embodiment, a dysphotopsia reducing intraocular lens may be comprised of an optic configured for implantation in the eye of a patient, the optic having anterior surface and posterior surfaces intersected by an optical axis, the anterior and posterior surfaces being joined by a transition area disposed about the optical axis, wherein the transition area inclines posteriorly from the anterior surface and intersects the anterior surface at an angle greater than approximately 40 degrees with respect to the optical axis. The rays of greatest divergence refracted into the eye by the cornea strike the anterior surface of the lens when implanted in the capsular bag of a patient's eye at the intersection of the first edge and the anterior surface. The rays of greatest divergence refracted into the eye by the cornea may be refracted by the anterior surface such that they are not incident on the first edge.

In another preferred embodiment, an intraocular lens may be comprised of an optic configured for implantation in the eye of a patient, the optic having anterior surface and posterior surfaces intersected by an optical axis, the anterior and posterior surfaces being joined by a peripheral region, the peripheral region inclined posteriorly from the anterior surface, the angle of inclination of the peripheral region being greater than $$sin^{-1}\left(\frac{n_2}{n_3}sinr_1\right),$$

where $n_3$ is the refractive index of the material of the intraocular lens, $n_2$ is the refractive index of aqueous humor and $r_1$ is the angle of refraction at which the most peripheral rays are refracted into the eye by the cornea.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Embodiments disclosed herein may be better understood from the following detailed description when read in conjunction with the accompanying drawings. Such embodiments, which are for illustrative purposes only, depict novel and non-obvious aspects of the inventions. The drawings include the following figures.

DETAILED DESCRIPTION OF THE PREFERRED EMBODIMENT

A human eye includes a transparent crystalline biconvex lens which can focus light from objects over a wide range of distances on the retina. The natural lens allows the eye to focus on the objects at various distances by changing its shape thereby changing its focal length. The ability of the lens to change its shape to adjust the focal length is known as accommodation. The lens is housed in a structure known as the capsular bag 102. During natural accommodation, the capsular bag is acted on by a ciliary muscle and zonular fibers (also known as zonules) in the eye, which can pull on the capsular bag to change its shape. The motion of the capsular bag generally deforms the lens in order to change its power, so that the eye can focus on objects at varying distances away from the eye.

In a healthy human eye ambient light is refracted into the eye by the cornea 101 and focused by the lens on the retina to form an image. The image is produced by the combination of the optical powers of the cornea 101, the capsular bag 102 and the lens, all of which are generally disposed about a central optical axis OA. As used herein, an "anterior direction" is in the direction generally toward the cornea, while a "posterior direction" is generally in the direction toward the retina which is located rearward of the cornea 101.

In a healthy human eye, an iris is disposed between the cornea 101 and the capsular bag 102 which provides a variable pupil that dilates under lower lighting conditions (scotopic vision) and constricts under brighter lighting conditions (photopic vision) to control the amount of ambient light that enters the eye.

The average diameter of the cornea in a human eye is between about 10 mm and 12 mm. The radius of curvature of the cornea is typically between about 6 mm and about 11.5 mm. The average distance between the mid-point of the cornea and the capsular bag is between about 2.0 mm and 5.0 mm. In general, the average horizontal diameter of the natural lens is between 9-10 mm and the average thickness of the natural lens is about 4.5 mm. The pupil diameter can vary between about 1.0 mm and about 8 mm.

Figure 1:
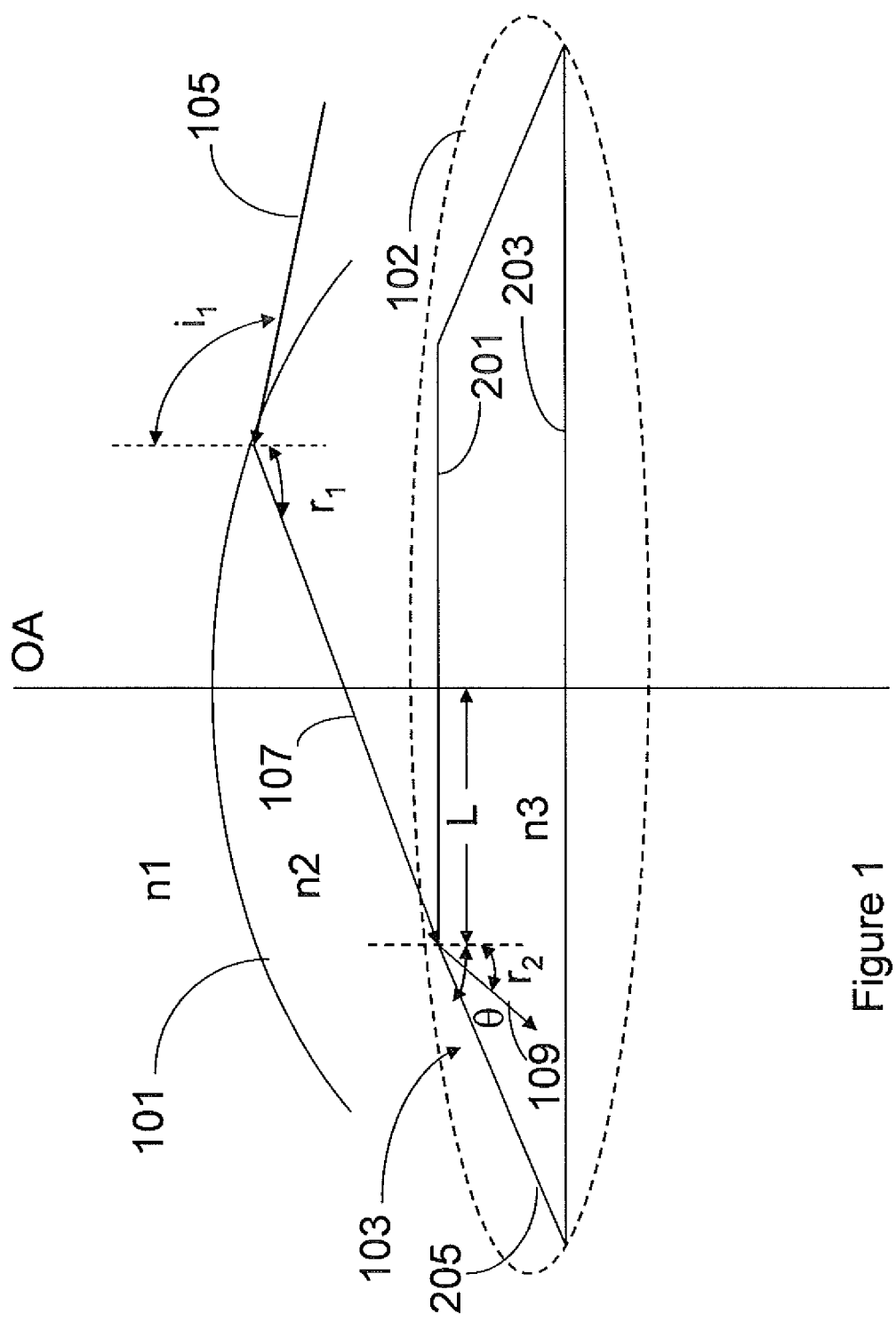
FIG. 1 is a schematic representation of certain aspects of a human eye with an artificial IOL positioned therein configured such that the most peripheral rays that enter the eye are incident on and anterior optical surface of the IOL and not incident on a peripheral region, such as an edge of the IOL.
Figure 2:
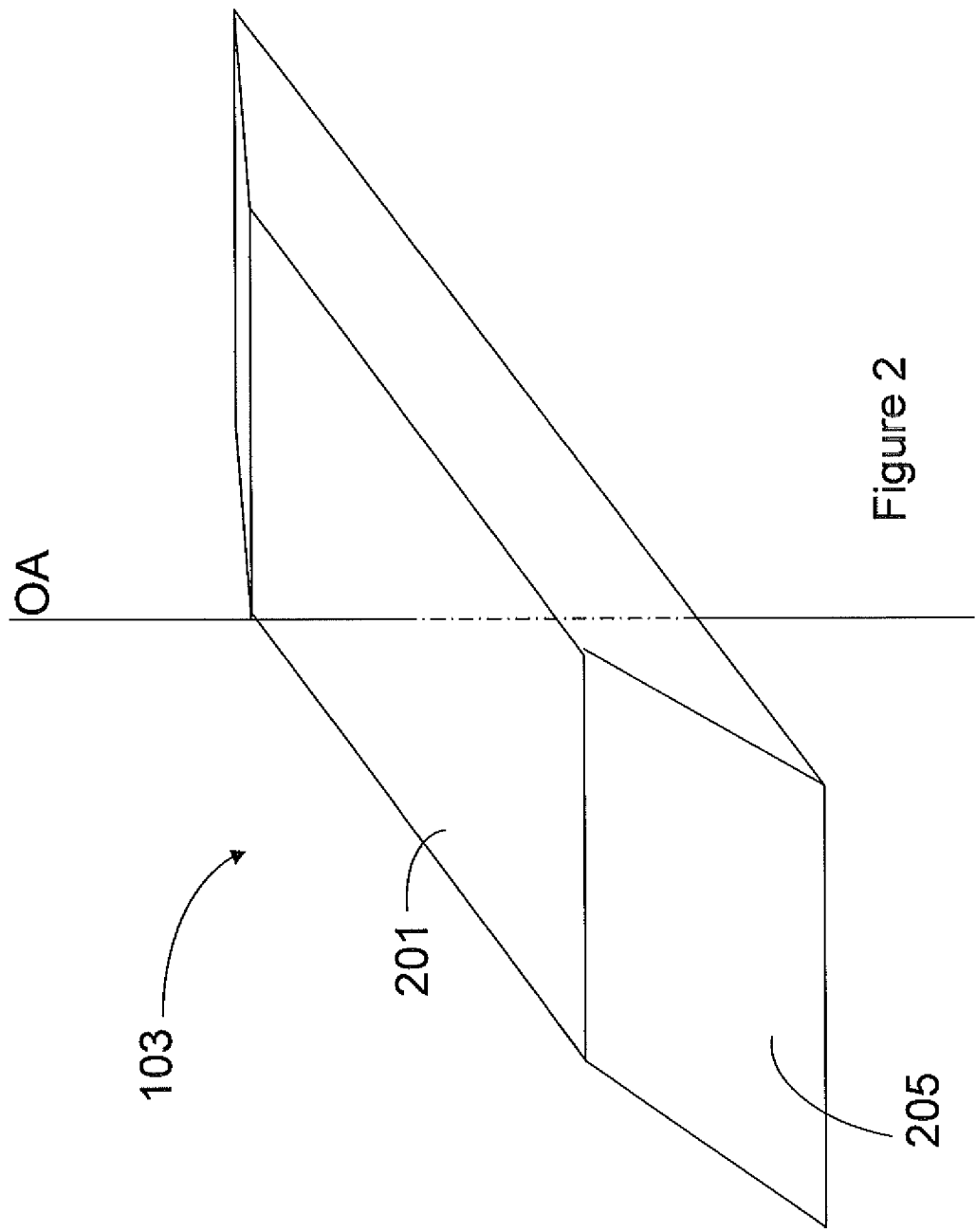
FIG. 2 is a schematic perspective view of an implementation of the IOL depicted in FIG. 1, showing a central optical axis.

FIG. 1 illustrates a cross-sectional view of a human eye in which an IOL 103 is implanted in the capsular bag 102 to replace the natural lens. FIG. 2 is a schematic perspective view of the implementation of the IOL 103 illustrated in FIG. 1. Although, the IOL 103 is illustrated as being implanted in the evacuated capsular bag 102, it is understood by a person having ordinary skill in the art that the IOL 103 can be a phakic/piggy-back IOL which acts as a secondary lens in a phakic eye that includes the natural lens. Also, it will be understood that the IOL 103 may have haptics (not shown) to mechanically position the optic in position in the eye. The IOL 103 has an anterior surface 201 and a posterior surface 203 that is intersected by the central optical axis OA. In use, the optical axis OA may extend from the fovea of the retina to an object being viewed. The IOL 103 also includes a peripheral region 205 that is disposed between the anterior surface 201 and the posterior surface 203. The peripheral region 205 can join the anterior surface 201 and the posterior surface 203. In various implementations, the peripheral region 205 may comprise a circular, elliptical or other regular shaped peripheral zone that extends posteriorly from the anterior surface 201.

Figure 3:
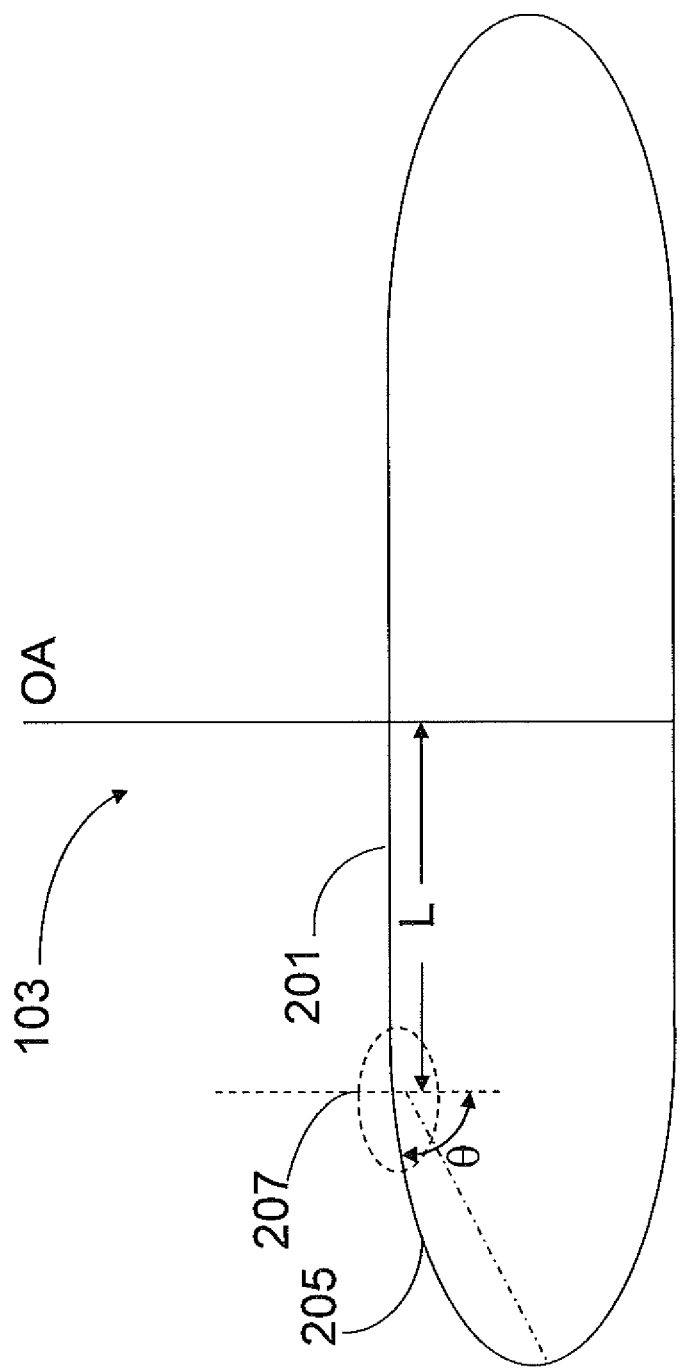
FIG. 3 is a cross-sectional view of another implementation of an IOL in which the most peripheral rays that enter the eye and are incident on and refracted by the IOL are not incident on an edge of the IOL.

The figures suggest that a very precise demarcation can be provided between discrete regions of the IOL 103, such as between the anterior zone 201 and the peripheral region 205. However, in some embodiments, a gradual transition can be provided between these and other zones. For example, in various implementations, the peripheral region 205 can include an inflection region 207 (illustrated in FIG. 3) that forms a transition area between the anterior surface and the peripheral region 205. The inflection region 207 may be inclined posteriorly with respect to the anterior surface 201 as discussed above. In various implementations, the inflection region can include a peripheral surface which connects the anterior surface 201 to the peripheral region 205.

The IOL 103 is generally made of a transparent biocompatible material that can be deformed. For example, in various implementations, the IOL 103 can be made of silicone or acrylic. The anterior and/or the posterior surface of the IOL 103 are curved such that the IOL 103 has optical power. The anterior and/or posterior surface may also be comprised of a diffractive surface. Or, the lens may be moveable with respect to the retina or other surface or deform to have adjustable power, as in an accommodating IOL.

The field-of-view of an average human eye is about 110 degrees in the horizontal direction. Accordingly, the most peripheral rays of light are incident on the cornea 101 at a maximum angle $i_1$ of about 110 degrees with respect to the central optical axis OA, as illustrated by ray 105, and are refracted by the cornea 101 into the eye, as illustrated by ray 107. Peripheral rays that are incident on the cornea 101 at an angle greater than about 110 degrees with respect to the central optical axis OA will not enter the eye, which is the reason for the limited field-of-view of the human eye. Rather, these rays will be reflected by or pass through the opposite side of the cornea. If the geometry of the cornea at the incident point of ray 105 and the refractive index of the cornea 101 and aqueous humor are known, the angle of refraction $r_1$ of the refracted ray of light 107 can be determined from Snell's law of refraction. Mathematically, Snell's law of refraction is expressed as $$\frac{\sin i}{\sin r} = \frac{n_2}{n_1},$$

where i is the angle of incidence of a ray of light that is incident from a medium having a refractive index $n_1$ onto a medium having refractive index $n_2$ and r is the angle of refraction. With reference to FIG. 1, $n_1$ is the refractive index of air which is considered to be 1.0 and $n_2$ is the combined refractive index of the cornea and the aqueous humor which is about 1.38. For a typical human eye, the most peripheral rays (e.g. ray 105) that are incident at an angle of about 110 degrees with respect to the central optical axis OA are refracted by the cornea 101 into the eye with an angle of about 80 degrees. In other words, for a typical human eye, $r_1$ is about 80 degrees.

The most peripheral rays that are refracted into the eye by the cornea (e.g. ray 107) are incident on the anterior surface 201 of the IOL 103 and refracted into IOL 103 in accordance with Snell's law of refraction, as illustrated by ray 109. The angle $r_2$ that ray 109 makes with respect to an axis parallel to the central optical axis OA, intersecting the peripheral region at the inflection point and extending in the posterior direction from the inflection point can be calculated from Snell's law of refraction if the geometry of the IOL 103 at the incidence point of ray 107 and the refractive index of the material of the IOL 103 is known. For the implementation illustrated in FIG. 1, the angle $r_2$ is given by $$\sin^{-1}\left(\frac{n_2}{n_3}\sin r_1\right),$$

where $n_3$ is the refractive index of the material of the IOL 103. Generally, for an acrylic or silicone IOL with a low refractive index, the angle $r_2$ is less than or equal to about 40 degrees for a typical human eye having $r_1$ of about 80 degrees.

In the embodiment of FIG. 1, the IOL 103 is configured such that the peripheral region 205 is disposed laterally of the point of incidence of the ray 107 with the anterior surface 201 of the IOL 103. Additionally, the peripheral region 205 is disposed away from the trajectory of the refracted ray 109. In other words, the ray 109 may be refracted by the IOL 103 along a path therethrough but the path does not intersect the peripheral region 205. In one embodiment, the region 205 may be inclined posteriorly from the anterior surface 201 and is at an angle θ greater than or equal to about 40 degrees and is preferably greater than or equal to about 55 degrees, and more preferably greater than or equal to about 60 degrees. The peripheral region may be substantially straight thus maintaining this angle. Or if the peripheral region is comprised of a curved portion, it may be configured such that light rays will not strike the peripheral region of the IOL. In other words, the most peripheral rays that enter the eye and are refracted into the IOL 103 would not be incident on peripheral region 205 and also would not be refracted by the IOL to pass through the peripheral region 205. Thus, the interaction between the light that is refracted into the IOL 103 and the peripheral region 205 can be reduced or eliminated which can prevent aberrant optical effects such as positive and/or negative dysphotopsia. Since, the angle of inclination θ of the peripheral region 205 depends on the phenomenon of refraction, in various implementations of the IOL 103, the angle of inclination θ of the peripheral region 205 is determined by the refractive index of the material of the IOL 103 and the geometry of the portion of the anterior surface 103 at which the most peripheral rays that enter the eye are incident. For a typical silicone or acrylic IOL, the angle θ may be in the range of about 40 degrees and 120 degrees, and is preferably in the range of about 40 degrees and 60 degrees, and more preferably in the range of about 55 degrees and 60 degrees.

As discussed above, one of the causes for negative dysphotopsia in some IOL designs is the creation of a shadow in the eye. The shadow can be in a region of the retina between two groups of rays that are incident on the retina. The first group of rays pass laterally of the IOL are not refracted at all by the lens. The second group of rays, which are immediately adjacent to the first group, are incident on the lens and are refracted at an angle away from the first group. This causes the two groups of rays to diverge, with little or no light being present in the region between the diverging rays. Thus, the region between the diverging rays is darker, i.e., a shadow is cast on the retina. The IOL 103 is configured such that the inflection region or the transition area 207 that is inclined posteriorly from the anterior surface 201 is disposed at a distance L from the central optical axis OA. If angle θ is greater than 90 degrees, then at least a portion of the inflection region or the transition area is inclined anteriorly. The distance L is selected to be equal to or greater than the outermost point of incidence of the ray 107. This ensures that the most peripheral rays that enter the eye are incident on the anterior surface and not on the peripheral zone 205. In such implementations, negative dysphotopsia can also be reduced or mitigated since all light that enters the eye is incident on the anterior surface of the IOL 103 and refracted in the preferred way. In various implementations, the inflection region can be disposed at a distance L of about 2-5 mm from the central optical axis OA.

Although FIGS. 1 and 2 illustrate the IOL 103 to be polygonal in shape, a person having ordinary skill in the art would understand that the anterior surface 201, the posterior surface 203 and the peripheral region 205 can be curved to produce the desired power. In various implementations, the anterior surface 201 or the inflection region can have some curvature. In those implementations, where the peripheral region 205 is arcuate, the angle of the inclination of the peripheral region 205 can be taken as the angle between an anterior-posterior line parallel to the central optical axis and a line connecting a point of inflection of the peripheral region 205 closer to the anterior surface and a point located at the boundary between the peripheral zone 205 and the posterior surface 203. In some implementations, where the peripheral region 205 is arcuate, the angle of inclination of the peripheral region 205 can be taken as the angle between the largest chord of the peripheral region 205 and an axis that is parallel to the central optical axis and extends posteriorly from the point of inflection.

In various implementations, the IOL 103 can be designed by selecting parameters such as the lateral distance of the peripheral region 205 from the central optical axis, the curvature of the peripheral region 205, the angle of inclination of the peripheral region 205 such that the most peripheral rays that enter an average human eye are incident on the anterior surface of the IOL 103 and do not intersect the peripheral region 205 after being refracted by the IOL 103. In some implementations, the IOL 103 can be designed specifically for a patient's eye by taking the patient's pupil diameter, depth of the capsular bag from a mid-point of the cornea into consideration such that most peripheral rays that enter the patient's eye are incident on the anterior surface of the IOL and do not intersect the peripheral region 205 after being refracted by the IOL. In other implementations, a set of IOLs designed for different pupil diameters and different depth of the capsular bag from a mid-point of the cornea can be provided to suit the needs of the general population.

The above described design considerations can also be used to design implementations or contact lenses, spectacles or other ophthalmologic visual aid devices to avoid aberrant optical effects.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intraocular lens comprising:
 an anterior optical surface extending peripherally from a central optical axis of the intraocular lens;
 a posterior optical surface extending peripherally from the central optical axis; and
 a peripheral zone disposed about and extending laterally from the anterior optical surface, the peripheral zone comprising an arcuate peripheral surface inclined posteriorly from the anterior optical surface and defining an interior angle greater than 60 degrees between a largest chord of the peripheral zone and a line extending posteriorly that is parallel to the central optical axis;
 wherein the interior angle of the arcuate peripheral surface is configured to prevent aberrant optical effects from high angle optical rays directed posteriorly toward the intraocular lens and refracted by the anterior surface and to prevent the high angle optical rays refracted by the anterior surface from passing through the peripheral zone, and
 wherein the intraocular lens is configured for a patient's eye, having a pupil diameter, a corneal mid-point, and a capsular bag depth from the corneal mid-point, by factoring the pupil diameter and capsular bag depth from the corneal mid-point such that most peripheral rays that enter the eye are incident on the anterior optical surface and do not intersect the peripheral zone after being refracted by the intraocular lens.

2. The intraocular lens of claim 1, wherein the arcuate peripheral surface extends laterally and posteriorly from a point of inflection disposed between the anterior surface and the peripheral zone and that the line extends posteriorly from the point of inflection.

3. The intraocular lens of claim 2, wherein the point of inflection is disposed laterally from the central optical axis by a distance in a range from 2 mm to 5 mm.

4. An intraocular lens comprising:
 an anterior optical surface extending peripherally from a central optical axis of the intraocular lens;
 a posterior optical surface extending peripherally from the central optical axis; and
 an arcuate peripheral surface disposed about and extending laterally from the anterior optical surface, the arcuate peripheral surface being inclined posteriorly from the anterior optical surface and defining an interior angle greater than 60 degrees between a largest chord of the peripheral zone and a line extending posteriorly that is parallel to the central optical axis;

wherein a transition between the anterior optical surface and the arcuate peripheral surface is spaced from the central optical axis by a distance of at least 2 mm, wherein the distance between the transition and the central optical axis is configured to cause peripheralmost light rays in a field-of-view of a patient to be refracted by the anterior optical surface when the intraocular lens is implanted in an eye of the patient, wherein the intraocular lens is configured for a patient's eye, having a pupil diameter, a corneal mid-point, and a capsular bag depth from the corneal mid-point, by factoring the pupil diameter and capsular bag depth from the corneal mid-point, and wherein the interior angle of the arcuate peripheral surface is configured to minimize dysphotopsia by preventing the peripheralmost light rays refracted by the anterior optical surface from passing through the arcuate peripheral surface of the lens.

5. The intraocular lens of claim 4, wherein the intraocular lens is configured to minimize negative dysphotopsia.

6. The intraocular lens of claim 4, wherein the intraocular lens is configured to minimize positive dysphotopsia.

7. The intraocular lens of claim 4, wherein the peripheral surface is located laterally outward of the trajectory of light rays refracted by the anterior surface of the lens.

8. A dysphotopsia reducing intraocular lens comprising:
an optic configured for implantation in an eye of a patient, the optic having anterior surface and posterior surfaces intersected by an optical axis, the anterior and posterior surfaces being joined by an arcuate transition area disposed about the optical axis, wherein the arcuate transition area inclines posteriorly from the anterior surface and intersects the anterior surface and defines an interior angle greater than 60 degrees between a largest chord of the transition area and a line extending posteriorly that is parallel to the optical axis, wherein the dysphotopsia reducing intraocular lens is configured for the eye of the patient by factoring the pupil diameter and capsular bag depth from the corneal mid-point, and wherein the interior angle of the transition area is configured to minimize dysphotopsia by preventing light rays from passing through the transition area of the lens.

9. The intraocular lens of claim 8, wherein rays of greatest divergence refracted into the eye by the cornea strike the anterior surface of the lens when implanted in the capsular bag at the intersection of a first edge and the anterior surface.

10. The intraocular lens of claim 9, wherein rays of greatest divergence refracted into the eye by the cornea is refracted by the anterior surface such that they are not incident on the first edge.

11. An intraocular lens comprising:
an optic configured for implantation in the eye of a patient, taking the eye's pupil diameter and depth of the eye's capsular bag from a mid-point of the eye's cornea into consideration, the optic having anterior surface and posterior surfaces intersected by an optical axis, the anterior and posterior surfaces being joined by an arcuate peripheral region, the arcuate peripheral region inclined posteriorly from the anterior surface and defining an interior angle between a largest chord of the transition area and a line extending posteriorly that is parallel to the optical axis, the interior angle of the arcuate peripheral region being greater than $$sin^{-1}\left(\frac{n_2}{n_3}sinr_1\right)$$

where $n_3$ is a refractive index of a material of the intraocular lens, $n_2$ is a combined refractive index of a cornea and an aqueous humor of the patient, the combined refractive index being 1.38, and $r_1$ is an angle of refraction at which the most peripheral rays are refracted into the eye by the cornea, the angle of refraction being 80 degrees, and wherein the angle of inclination of the arcuate peripheral region is configured to minimize dysphotopsia by preventing light rays from passing through the peripheral region of the lens.

* * * * *